United States Patent
Xuan et al.

(10) Patent No.: US 7,732,564 B2
(45) Date of Patent: Jun. 8, 2010

(54) SERUM TUMOR MARKER IN RODENT PROSTATE CANCER MODELS

(75) Inventors: Jim W. Xuan, London (CA); Joseph L. Chin, London (CA)

(73) Assignee: London Health Sciences Centre Research Inc., London, Ontario (CA)

( * ) Notice: Subject to any disclaimer, the term of this patent is extended or adjusted under 35 U.S.C. 154(b) by 678 days.

(21) Appl. No.: 11/412,869

(22) Filed: Apr. 28, 2006

(65) Prior Publication Data

US 2006/0246521 A1     Nov. 2, 2006

Related U.S. Application Data

(60) Provisional application No. 60/675,448, filed on Apr. 28, 2005.

(51) Int. Cl.
*C07K 5/00*     (2006.01)
(52) U.S. Cl. .................................................. 530/300
(58) Field of Classification Search ............. None
See application file for complete search history.

(56) References Cited

OTHER PUBLICATIONS

Kwong et al (Prostate. Feb 15, 2000;42(3):219-29.*
Hara, M. And Kimura, H., J Lab.Clin.Med, 113: 541-548, 1989.
Abrahamsson, P.-A. et al., The prostate, 12: 39-46, 1988.
Hyakutake, H. et al., The prostate, 22: 347-355, 1993.
Grande, M. et al., Clin. Cancer Res., 6: 1790-1795, 2000.
Stege, R. et al., Clin. Cancer Res., 6: 160-165, 2000.
Xuan, J.W. et al., DNA Cell Biol, 18: 11-26, 1999.
Gabril, M. Y. et al., Gene Therapy, 9: 1589-1599, 2002.
Imasato, Y. et al., J.Urol., 164: 1819-1824, 2000.
Bauman, G. S. et al., Prostate J, 2: 94-101, 2000.
Thota, A. et al., J.Cell Biochem., 88: 999-1011, 2003.
Hara, M and Kimura, H., J Lab.Clin.Med, 113:541-548, 1989.
Abrahamsson, P.-A. et al., The prostate, 12:39-46, 1988.
Hyakutake, H. et al., The prostate, 22:347-355, 1993.
Imasato, Y. et al., Prostate J., 2: 94-101, 2000.

* cited by examiner

*Primary Examiner*—Christopher H Yaen
(74) *Attorney, Agent, or Firm*—Bereskin & Parr LLP/S.E.N.C.R.L., s.r.l.; Micheline Gravelle

(57) ABSTRACT

The present invention relates to a rodent serum marker for prostate cancer comprising b-microseminoprotein (PSP94) and diagnostic methods thereof. The present invention also relates to a recombinant sequence to raise a ligand of a specific binding affinity to a rodent serum marker for prostate cancer, which comprises the following amino acid sequence:

(SEQ ID NO: 1)
MGGSHHHHHHGMASMTGGGMGRNTRYDDDDKDRWGSWVCSIENREIFPN
QMSDDCMDADGNKHFLNTPKKNCTWCSCDKTSITCCTNATPLSYDKDNCD
VQFHPENCTYSVVDRKNPGKTCRVDSWTM.

1 Claim, 8 Drawing Sheets

Figure 2
PSP94 staining intensity and extent
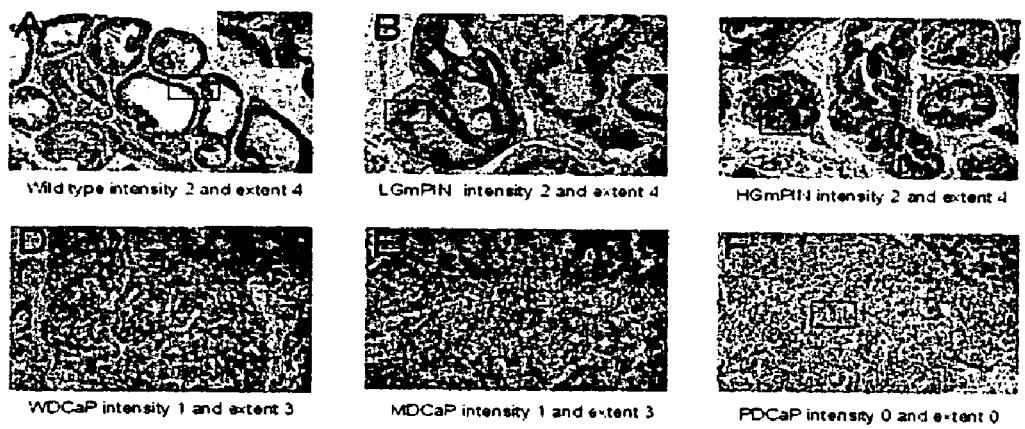
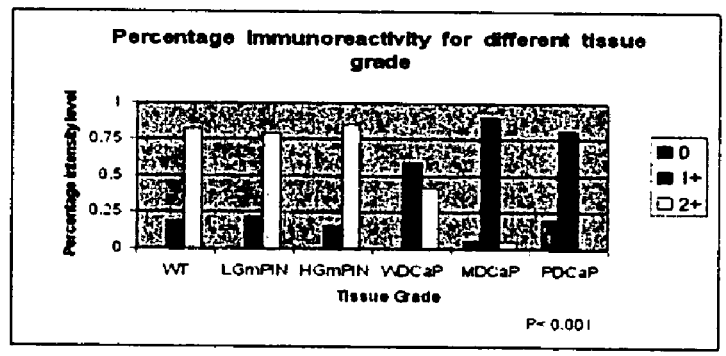

Figure 5
A. Competitive ELISA standard curve: pTrcHis mPSP94 as competitor
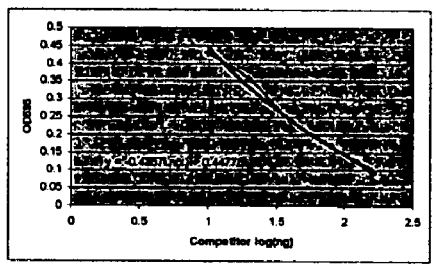
B. Competitive ELISA standard curve: mPSP94 from VP lysate as competitor
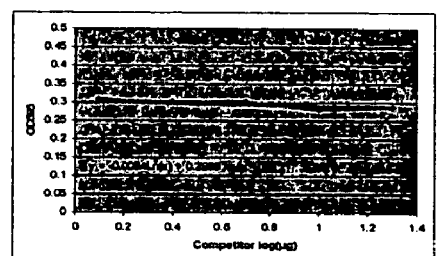
C. Competitive ELISA standard curve: pTrcHis mPSP94 as competitor and blocked with *E. coli* lysate
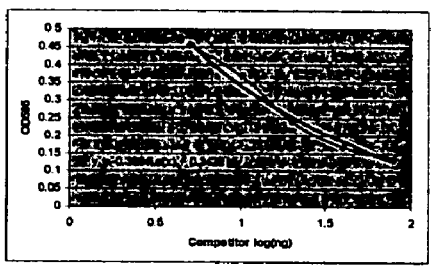
D. Competitive ELISA standard curve: mPSP94 from VP lysate as competitor and blocked with *E. coli* lysate
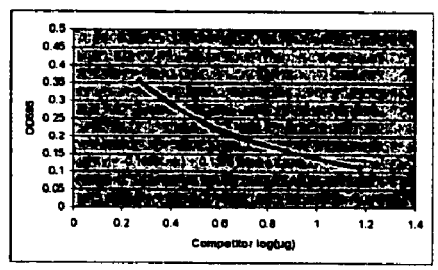

A  Lonitudinal serum mPSP94 levels following hormone therapy of KIMAP

B  Histology/IHC

SERUM TUMOR MARKER IN RODENT PROSTATE CANCER MODELS

FIELD OF THE INVENTION

The present invention relates to novel serum marker in rodent prostate cancer models.

BACKGROUND OF THE INVENTION

There were an estimated 220,900 new cases of prostate cancer (CaP) and 28,900 deaths in the US in 2003. Prostate cancer remains the most frequently diagnosed malignancy among North American males, and is second only to lung cancer in mortality. Genetics, diet, and lifestyle are just some of the factors that contribute to the development of prostate cancer. Prostate specific antigen (PSA) is the only prostate cancer marker widely used for population screening, diagnosis, and monitoring of prostate cancer (prostate cancer). The use of PSA as a serum marker has increased our ability to detect Prostate cancer, select therapy and to monitor outcomes.

Prostate cancer has proven to be a complicated disease due to its heterogeneous and multifocal nature. Consequently, much research has been devoted to elucidating the mechanisms of the disease. This has led to the construction of genetically engineered mouse models of prostate cancer utilizing transgenic and knock-out techniques that attempt to model the human clinical situation in all aspects. Rat probasin gene-based transgenic adenocarcinoma prostate (TRAMP) and LPB-SV40 tag (LADY) models are currently the most prevalent murine prostate cancer models.

Unlike in humans, murine models of prostate cancer currently lack established biomarkers for the disease, specifically serum biomarkers. Current prostate cancer (CaP) research in both basic and pre-clinical trial studies employ genetically engineered (GE) mouse models, since CaP does not occur naturally in rodents.

A serum biomarker in genetically engineered (GE)-CaP is valuable in four ways: it enables the non-invasive detection of cancer stage/progression; it can be used to assess effectiveness of treatments; it can monitor disease recurrence/disease-free state; and it is a much more affordable alternative than expensive molecular/micro-imaging techniques. The ability to non-invasively quantify tumor burden in living conditional tumor model mice will ultimately lead to the development of more accurate models of human cancer that are better suited to evaluating and optimizing preclinical cancer therapy.

Since mice do not produce and express a human PSA analog, the search begins for other equals in mice. Prostatic secretory protein of 94 amino acids (PSP94), also known as β-microseminoprotein (β-MSP) (Hara, M. and Kimura, H., J Lab .Clin. Med, 113: 541-548, 1989; Abrahamsson, P.-A. et al., The prostate, 12: 39-46, 1988; Hyakutake, H. et al., The prostate, 22: 347-355, 1993), is one of the three most abundantly secreted proteins from the prostate gland (the others being PSA and PAP [prostatic acid phosphatase]). Though PSP94 is an abundant protein, little is known about its real biological function. As with PSA, much research has investigated the utility of PSP94 as a prostate cancer marker in humans in terms of serum bound/free forms, urine levels and tissue expression. Furthermore, PSP94 expression in prostate tissue has been demonstrated as having statistical association with histological grade. In most cases this association is inversely correlated—that is, as tumor grade advances PSP94 expression decreases (Hyakutake, H. et al., The prostate, 22: 347-355, 1993)—the same as in PSA (Grande, M. et al., Clin. Cancer Res., 6: 1790-1795, 2000; Stege, R. et al., Clin. Cancer Res., 6: 160-165, 2000).

It would be highly desirable to be provided with a serum marker in rodent prostate cancer models.

SUMMARY OF THE INVENTION

In accordance with the present invention, there is provided a serum marker in rodent prostate cancer models and uses thereof.

In accordance with the present invention, there is provided a rodent serum marker for prostate cancer comprising β-microseminoprotein (PSP94).

Preferably, the marker of the present invention is glycosylated β-microseminoprotein (PSP94).

In accordance with the present invention, there is provided a recombinant sequence to raise a ligand of a specific binding affinity to a rodent serum marker for prostate cancer, which comprises the following amino acid sequence:

```
                                            (SEQ ID NO: 1)
MGGSHHHHHHGMASMTGGGGMGRNTRYDDDDKDRWGSWVCSIENREIFPN
QMSDDCMDADGNKHFLNTPKKNCTWCSCDKTSITCCTNATPLSYDKDNCD
VQFHPENCTYSVVDRKNPGKTCRVDSWTM.
```

Preferably, the rodent is a mouse.

In accordance with the present invention, there is provided a ligand of a specific binding affinity to a rodent marker of the present invention, preferably raised against the recombinant sequence of the present invention.

Preferably, the ligand of the present invention is selected from the group consisting of polyclonal antibody, monoclonal antibody and binding fragments thereof.

In accordance with the present invention, there is provided a method for the detection of PSP94 presence in serum sample of rodent, which comprises:

a) contacting the serum sample with a ligand of the present invention; and b) determining the presence of PSP94 bound to the ligand.

Preferably, step b) is qualitative or quantitative.

In accordance with the present invention, there is provided a method of identifying different grade of cancer, which comprises comparing a determined level of PSP94 in serum sample with a calibration curve and wherein a decrease in PSP94 is indicative of prostate cancer progression. Preferably, the level of PSP94 is determined using the method of the present invention.

In accordance with the present invention, there is provided a kit for pre-clinical trials using rodent prostate cancer model, which comprises:

a) a ligand of the present invention; and b) means to determine the presence of PSP94 bound to the ligand of step a).

Preferably, the kit of the present invention further comprises:

c) means to quantify the presence of PSP94 compare to a standard calibration curve of control subjects.

In accordance with the present invention, there is provided a method to screen for candidate drugs as therapy of prostate cancer, which comprises the steps of:

a) administering the candidate drug to a rodent prostate cancer model; and b) means to monitor a level of PSP94 in serum sample and wherein a substantial decrease in PSP94 is indicative of a drug being a potent therapy for prostate cancer.

All references referred herein are hereby incorporated by reference.

BRIEF DESCRIPTION OF THE DRAWINGS

FIG. 2 illustrates histological analysis of prostate tissue PSP94 expression from GE-CaP mouse models. (A) Strong PSP94 expression (2+) in wild-type prostate tissue with a 76-100% extent of staining (20×). Inlet A is highlighting the stain free stroma (40×). (B) Strong PSP94 expression (2+) in LGmPIN prostate tissue with a 76-100% extent of staining (20×). Inlet showing the stained cytoplasm of the secretory cells where PSP94 is located (40×). (C) Strong PSP94 expression (2+) in HGmPIN area with an extent of 76-100% (20×). Arrow pointing to the stained cytoplasm of the secretory cells (40×). (D) Moderate intensity of PSP94 staining (1+) in well differentiated CaP with an extent of 51-75% (20 ×). At higher magnification (40×), nuclear atypia is clear as well as staining localization of PSP94 to the cytoplasm of the secretory cells. (E) Moderate intensity of PSP94 staining (1+) in moderately differentiated CaP with an extent of 51-75% (20 ×). Inlet showing boxed area of nuclear atypia and proliferating cells with weaker staining localized in the cytoplasm of the secretory cells (by arrow). (F) Negative PSP94 expression (0) in poorly differentiated CaP with higher magnification revealing nuclear atypia (arrow B) and cell proliferation (arrow A). (G) Graph showing the correlation of immunoreactivity with CaP progression. WT=normal wild type mice, LGmPIN=lowgrade mouse PIN, HGmPIN=high-grade mouse PIN, WDCaP=well differentiated CaP, MDCaP=moderately differentiated CaP, and PDCaP=poorly differentiated CaP. Difference between grade and immunoreactivity is significant (P<0.001).

FIG. 5 illustrates the establishment of standard curves for quantifying levels of serum PSP94 by a competitive ELISA (enzyme linked immunosorbent assay) protocol. Recombinant pTrcHis mPSP94 was used as a coating agent (100 ng/well) in 96 wells plates. A competitive reaction (see M&M) with varying amounts of standardized competitor protein as indicated on the x-axis (logng) was pre-incubated with PSP94 polyclonal antibody (1:40,000 dilution) and added to the coated wells. (A) Standard competitive ELISA curve with pTrcHis mPSP94 protein as competitor. (B) Standard competitive ELISA curve with natural mouse PSP94 from ventral prostate tissue lysate as competitor (VP lysate=100 μg/μl). (C) Similar competitive ELISA as in graph A, but polyclonal mouse PSP94 antibody was competed (blocked) with *E. coli* cell (DH5α) lysate to remove the dominant antibodies for carrier protein isomerase. This type of standard competitive ELISA curve was used for quantifying levels of mouse serum PSP94. (D) According to standard curve of C, one example of the competitive ELISA assays ability to detect natural mouse PSP94 in VP lysates (by logμg). Logarithmic line (in bold) of the best fit (MS Excel) used to interpolate unknown PSP94 levels from serum samples.

DETAILED DESCRIPTION OF THE INVENTION

Figure 1:
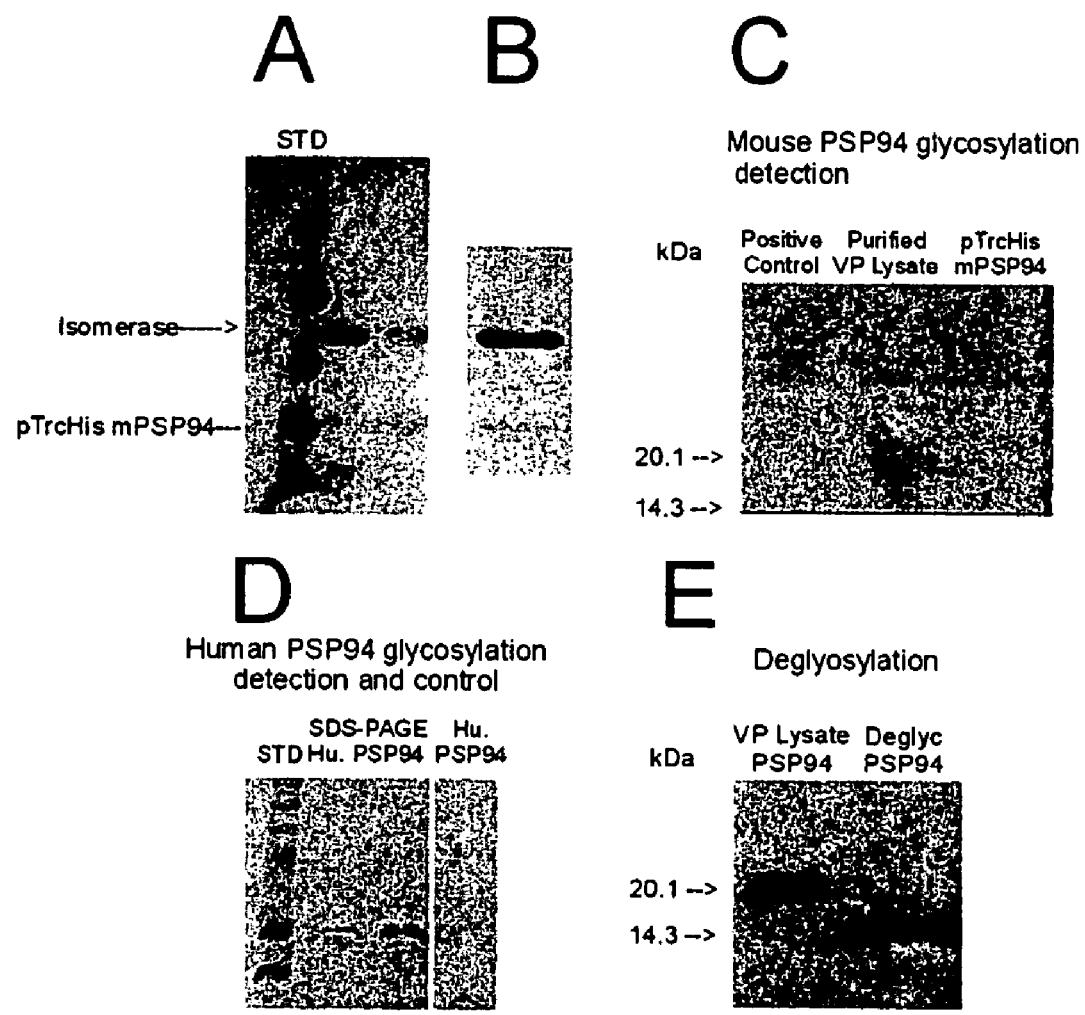
FIG. 1 illustrates that mouse prostate tissue PSP94 is glycosylated as demonstrated by a polyclonal antibody against recombinant pTrcHis mouse PSP94. (A) SDS-PAGE and Coomassie Blue staining (A) and Western blotting (B) analyses of the purified recombinant pTrcHis mPSP94 (lower band). Recombinant mouse PSP94 is shown at apparent molecula weight of ~15 kDa. (C) Demonstration of glycosylation of mouse prostate tissue (VP) PSP94 protein. All samples were purified using a polyclonal mouse PSP94 antibody (see M&M and FIG. 2). Magenta staining indicates protein glycosylation is positive. The positive glycosylation control protein (horseradish peroxidase, left lane) was provided by the kit (see M&M). Ten μg of pTrcHis mPSP94 (right lane) and purified human (Hu) seminal PSP94 26, 27 were loaded as negative controls. (D) SDS-PAGE showing the purified human seminal PSP94 (5, 10 pg each lane), loaded as a comparison for glycosylation tests. (E) Western blotting showing the de-glycosylation test of mouse prostate PSP94 in the prostate tissue lysate (10 μl/lane loaded from a lysate of 100 mg wet weight/ml). Gel was run for a shorter period of time and so (VP) PSP94 band has less smearing. Prestained standard protein ladder (STD, Invitrogen) used are (from bottom): 8.4, 14.9, 19.6, 26, 37.4 kDa.

In accordance with the present invention, there is provided a mouse serum tumor marker from a mouse homologue of human PSP94 (prostate secretory protein of 94 amino acids). PSP94 is one of the three most abundantly secreted proteins from the prostate and, as with PSA, is one of the clinical biomarkers of human prostate cancer. An antibody was first raised against recombinant mouse PSP94 and characterized with high titer and tissue specificity. With this antibody, mouse PSP94 was discovered to differ from human PSP94 in that it is glycosylated. Immunohistochemistry studies on different histological grades of mouse GE-CaPs from both transgenic and knock-in mouse prostate cancer models demonstrated the association of the down regulation of tissue PSP94 expression (P<0.001), the same as for PSA and PSP94 in humans. The presence of mouse serum PSP94 was demonstrated by affinity column and immuno-precipitation purification utilizing a polyclonal mouse PSP94 antibody. A competitive ELISA (enzyme linked immunosorbent assay) protocol was established to quantify serum PSP94 levels with a sensitivity of 1 ng/ml. Quantified serum levels of mouse PSP94 ranged from 50 ng/ml in wild type mice to 150 ng/ml, 835.5 ng/ml, and 774.8 ng/ml in 20 week, 40 week and >40 week GE-CaP mice respectively. This increase in serum PSP94 is also correlated with tumor grade in these GE-CaP mice (P<0.001, n=68). Through longitudinal monitoring of serum PSP94 levels of castrated mice (androgen ablation therapy), we found a correlation between responsiveness/refractory prostate tissues and serum PSP94 levels. The utility of the mouse serum PSP94 marker in clinical trials of hormone therapy was further confirmed by 3-D ultrasound imaging on living mice in this study. The establishment of the first rodent prostate cancer serum biomarker will greatly facilitate both basic and pre-clinical research on human prostate cancer, the most common cancer in adult men in North America.

Materials and Methods

Expression and Purification of Polyhistidine Containing Recombinant Mouse PSP94:

A mouse PSP94 cDNA clone was isolated and sequenced as reported previously (Xuan, J. W. et al., DNA Cell Biol, 18: 11-26, 1999). A cDNA fragment coding for the mature form of mouse PSP94 was amplified and inserted into the polyhistidine containing vector (pTrcHis A, Invitrogen, Carlsbad, Calif.). The preparation of bacterial culture was performed in E. coli strain DH5 alfa and the induction of recombinant protein was by 100 mM IPTG when the cell culture reached an OD600 nm of 0.6 and continued incubation for another 2 hours at 37° C. Recombinant TrcHis-mPSP94 fusion protein was purified by a $NiSO_4$ charged-Sepharose based affinity column (His.Bind, Novagen) following manufacturer's recommendations. Because the yield is poor (<500 g/l), a large-scale (2 L NZCYM medium, Invitrogen) preparation of the fusion protein was conducted. The recombinant TrcHis-mouse PSP94 was purified by a denaturing method, i.e a 6M guanidine lysis buffer pH 7.8 was employed to dissolve both cytosol and the precipitated proteins in side E. coli cells. The total lysate proteins were loaded onto the Ni++ affinity column, and washed sequentially with a denaturing binding buffer (5 mM imidazole, 50 mM NaCl, 20 mM Tris-HCl pH.7.9) and a wash buffer (40 mM imidazole, 50 mM NaCl, 20 mM Tris-HCl pH.7.9), and the protein was then eluted with a buffer of 1 M imidazole, 500 mM NaCl, and 20 mM Tris-HCl, pH 7.9. The concentration of protein is measured at OD280 nm and confirmed with a molecular weight standard (Invitrogen) in 15% SDS-PAGE followed by staining with Coomassie Blue.

An E. coli strain DH5α (Invitrogen) was used to purify large amounts of recombinant protein. The preparation of bacterial culture and the induction of recombinant protein by 100 mM IPTG (isopropylthio-β-D-galactoside) were conducted accordingly 19. Recombinant pTrcHis-mouse PSP94 (pTrcHis-mPSP94) fusion protein was purified by a $NiSO_4$ charged Sepharose-based affinity column (His.Bind, Novagen, Madison, Wis.) following the manufacturer's recommendations. Because the yield was poor (150 g/L), a large-scale (20 liters of NZCYM medium, Invitrogen) preparation of the fusion protein was conducted. Large amounts of recombinant protein were harvested, pooled and aliquoted (400 ng/µl). The concentration of protein is measured at OD=280 nm and confirmed with a molecular weight standard (Invitrogen) in 15% SDS-PAGE followed by staining with Coomassie Blue. The exact quantification of the pooled recombinant protein was conducted repeatedly by Bradford protein assays (BioRad, Hercules, Calif.) and by densitometry analysis. Mass Spectrometry Matrix Assisted Laser Desorption/Ionization (MS-MALDI) protein sequencing was used for the identification of pTrcHis-Mouse PSP94. In brief, 10 µg of recombinant protein were run on 15% SDS-PAGE (polyacrylamide gel electrophoresis) and stained using Gel Code blue stain (BioRad). After destaining, the band was excised from the gel and in-gel trypsin digestion was performed. The sample was then subjected to MS analysis at the Biological Mass Spectrometry Laboratory of our university. For the sequencing, Electrospray Mass Spectrometry Time of Flight (ESI-QTOF) techniques were also performed. The resulting peptide sequences were then searched against mouse protein sequences (www.ncbi.nim.nih.gov) and found to be perfectly homologous to mPSP94 with a molecular mass of 14.6 kDa (93 amino acids plus 35 amino acids leading peptide in pTrcHis plasmid).

Generation of Rabbit Antiserum Against Recombinant Fusion Proteins of TrcHismPSP94:

Rabbit polyclonal antibodies against recombinant mouse PSP94 proteins were obtained using a standard procedure (SOP #370-01, University of Western Ontario Animal Care Committee). In brief, approximately 2.5 mg of recombinant mouse PSP94 (1.0 ml) was emulsified in 1.0 ml of Freund's adjuvant (incomplete, from Sigma, St. Louise, Mich.) and injected intramuscularly into rabbits 1 kg in size. A second booster (1.5 mg) injection was performed 2 weeks later. Adequate antibody activity was obtained within 1 month of the second injection.

Genetically Engineered (GE) Mouse Prostate Cancer Models:

In previous studies, we used a 3.84 kb promoter/enhancer region of the PSP94 gene directing the expression of an oncogene of SV40T/t antigen targeted specifically to the mouse prostate tissue (strain F1[C57BL/6×CBA]) to establish a GE-CaP model called PSP-TGMAP (PSP94-transgenic mouse of adenocarcinoma in the prostate). Similar to the TRAMP (Transgenic adenocarcinoma prostate) model, PSP-TGMAP mice developed fast-growing tumors specifically in the prostate within 4-8 months of age. In view of limitations of transgenic technique-derived CaP models, we established a knock-in mouse adenocarcinoma prostate model (PSP-KI-MAP) by targeting the SV40 Tag at a PSP94 gene, which demonstrated close-to-human CaP features. Both GECaP models developed prostate cancer after puberty in lobes of the ventral prostate (VP), dorsolateral prostate (DLP), and anterior prostate (CG [coagulating gland]).

Mouse Blood Collection, Animal Handling and Dissection, and Tissue Lysate Preparation:

Mice were anesthetized at a dose of 0.03 ml/10 g of a ketamine/xylazine mixture (anesthesia stock: 100 mg/ml ketamine and 20 mg/ml xylazine). Tail blood sample collection to a maximum volume of 300 ml at any one time from living mice was conducted with light anesthesia and following the published protocols 20 as per our UCAC approved protocol. When longitudinal samples were required, blood was removed via the tail every 2-3 weeks 20. When maximum blood samples were required, collection was through the chest cavity with deep anesthesia. Mouse prostate tissue anatomy was performed as previously reported. The urethra, vas deferens, prostate gland complex (VP, DLP and CG) and the seminal vesicles (SV) were dissected out from the anaesthetized adult animals. Tissue samples from the prostate and the male accessory gland were freshly dissected and homogenized in a lysis buffer: 1% sodium dodecyl sulphate (SDS), 1 mM phenylmethylsulfonylfluoride (PMSF), and 0.01 M phosphate buffered saline (PBS). For histological studies, fresh prostatic tissues were fixed in 10% Formalin (Fisher), treated with ethanol and xylene, and embedded in paraffin. All histological processing including hematoxylin and eosin (H&E) staining were conducted according to standard protocols in the pathology laboratory in our hospital. Orchidectomy (castration) operations were performed through scrotum access. All animal experiments were conducted according to protocols (including post operative care) approved by the University Council on Animal Care.

Histological Grading, Immunohistochemistry (IHC) and Immunostaining Evaluation:

Histological grading was performed according to the MMHCC (Mouse Models for Human Consortium Committee) Prostate Pathology Committee Bar Harbour Classification System and as previously reported (Gabril, M. Y. et al., Gene Therapy, 9: 1589-1599, 2002). Histopathological characterization and standard definitions of various degrees of mPIN (mouse prostatic intraepithelial neoplasia)—well, moderately and poorly differentiated CaPs—were classified as previously reported (Gabril, M. Y. et al., Gene Therapy, 9: 1589-1599, 2002). For IHC analyses, formalin fixed, paraffin embedded 4.0 µm sections were stained as previously reported. Specificity of the staining was confirmed by replacing the primary antibody with normal goat serum. Each IHC staining specimen was assessed independently by three authors (I.V.H., G.W., and M.M) and a consensus of grading was reached. The intensity of the staining was graded on a scale of 0 to 2+ indicating no staining and strong staining respectively as previously reported (Imasato, Y. et al., J.Urol., 164: 1819-1824, 2000). The extent of the staining in tumor foci was classified as 0%, 1-25%, 26-50%, 51-75%, and 76-100% as previously reported (Imasato, Y. et al., J.Urol., 164: 1819-1824, 2000). Antibodies used in this study were: high titer rabbit antiserum against recombinant mPSP94, monoclonal SV40 Tag oncogene (Calbiochem, CA), and androgen receptor (Affinity Bioreagents, Golden, Colo.). Dilution factors used were 1:5000, 1:100, and 1:250 respectively.

Preparation of Affinity Column Using Antiserum of Mouse PSP94, Immunoprecipitation, and Western Blotting:

pTrcHis-mPSP94 antiserum was coupled to a 1 ml HiTrap NHS-activated Sepharose High Performance column (Amersham Biosciences) in a standard coupling buffer (0.2 M NaHCO$_3$, 0.5 M NaCl, pH 8.3) for 30 minutes at room temperature. Several HiTrap NHS-activated Sepharose High Performance columns were coupled to varying amounts of antibody in order to optimize the columns ability to purify PSP94. It was determined that 1 ml of antiserum incubated in the column for only 30 minutes produced the best results. Purified IgG was used during the coupling process but demonstrated no significant difference in the ability to purify PSP94 compared to polyclonal antiserum and thus was not used. All uncoupled active groups were deactivated via alternating washes of Buffer A (0.5 M ethanolamine, 0.5 M NaCl, pH 8.3) and Buffer B (0.1 M acetate, 0.5 M NaCl, pH 4). The column was then equilibrated with a neutral buffer (Binding Buffer: 50 mM Tris, 0.15 M NaCl, pH 7). All samples tested were equilibrated with the binding buffer and passed through the column overnight at 4° C. at a flow rate of 1 ml/min. The column was then washed with binding buffer and eluted (Elution Buffer: 100 mM glycine, 150 mM NaCl, 1% Triton, pH3). The purified sample was then desalted using a HiTrap Desalting column (Amersham Biosciences). For Western blotting experiments, an ECL (enhanced chemiluminescent) method kit (Amersham, Oakville, Ontario, Canada) was used and an HRP (horse radish peroxidase) conjugated anti-rabbit IgG (rabbit IgG TrueBlot, from eBioscience) was used as a secondary antibody. Immuno-precipitation was performed using a Rabbit IgG TrueBlot set (eBioscience). Roughly 5 µg of pTrcHis polyclonal antibody was incubated with each sample and then added to 50 µl of anti-rabbit Ig IP beads. The beads were then washed with sample buffer (50 mM Tris HCl pH 8.0; 150 nM NaCl; 1% NP-40), boiled with an SDS loading buffer for 3 minutes, and loaded onto a 15% SDS-PAGE gel for Western blotting. Glycosylation detection of mouse PSP94 was performed using a commercial kit (Glyco-Pro, Sigma). Standard protocol for the kit was followed. Purified mouse PSP94 was run on a 15% SDS PAGE gel and the gel was oxidized, stained (Schiff), and reduced resulting in magenta staining of glycosylated proteins. De-glycosylation was performed using a commercial kit (Glyko, Prozyme, San Leandro, Calif.) and the denaturing protocol was followed. The protein was run on a 15% SDS PAGE gel as well and mouse PSP94 was detected via Western blot.

Establishment of a Competitive ELISA (Enzyme Linked Immunosorbent Assay) Protocol for Quantification of Serum PSP94:

Levels of serum PSP94 were quantified by a competitive ELISA as we previously reported (Bauman, G. S. et al., Prostate J, 2: 94-101, 2000). For all assays, recombinant pTrcHis mPSP94 was used as the coating antigen (100 ng/well). 96-well immunoplates (Nunc, Gibco/BRL, Mississauga, ON) were coated at 4° C. overnight in carbonate coating buffer (1.4 mM Na2CO3, 7 mM NaHCO$_3$, pH 9.2). The coated plate was washed three times in phosphate buffered saline (PBS-T) buffer and blocked in 1.5% bovine serum albumin (BSA, RIA grade, Sigma) in PBS-T at 37° C. for 1 h. PSP94 antiserum was diluted 1:40000 in 1.5% BSA/PBS-T with *E. coli* lysate and pre-incubated for 1 h. For preparation of *E. coli* DH5α lysates, 2 L of NZCYM medium culture were grown until an OD600 nm of 1.5 and then the bacteria pellet was homogenized in 10 ml of PBS following 3 freeze-thaw cycles. Blocked antiserum was then added to standards/samples and incubated for 1.5 hrs. Competitor mixtures were then added to immunoplates and incubated for 30 minutes. Competition reaction was stopped by washing three times in PBS-T. HRP conjugated swine antiserum antirabbit IgG was diluted and incubated for 1 h. The plate was then washed three times in PBS-T and incubated in 0.4 mg/ml OPD (o-phenylene diamine dihydrochloride, Sigma) and 0.05% $H_2O_2$ in developing buffer (35 mM citric acid, 67 mM $Na_2HPO_4$, pH 5.0) for 20 min. The color reaction was stopped by the addition of 1 N $H_2SO_4$. The optical density for each standard/sample was measured by a multi-well plate reader (Biorad) at OD595 and graphs were generated. Standard curves were plotted by relative absorbency (B/B0) against competitor standard protein (ng/ml). Relative absorbency (B/B0) was calculated as follows: B=OD492 of the sample-NSB. NSB (non-specific binding) was determined by testing OD492 with excess standard (1μg) in the competition reaction to entirely block the antibody, (i.e. under maximum competition and minimum antibody binding to the plate). BO=OD492 of the maximum antibody binding (no competition)—NSB.

Levels of Serum PSP94 Quantification:

Various mouse serum samples (50 μl/each well) were run in triplicate as described above, and protein concentrations were interpolated from the logarithmic equation for the corresponding trend line (e.g., y=−0.3364Ln(x)+0.3429). Mice were grouped according to age, which is synchronous with cancer progression in our KIMAP model. Twenty-week-old mice were characterized as normal/prostatic intraepithelial neoplasia mice of low grade and/or high grade. Forty-week-old mice were characterized as early stage CaP and >40-week-old mice as advanced CaP. Serum samples were obtained prior to castration when ultrasound detected a tumor roughly 4 mm in size. Serum samples were then harvested 2 and 5 weeks post castration in order to monitor a response of the cancer to androgen deprivation.

Three-Dimensional Ultrasound (3-D US) image acquisition:

We followed the following protocols. In brief, mice were anesthetized by inhalation of 2% isoflurane in oxygen and restrained on a heated stage (THM-100, Indus Instruments, Houston, Tex.) during imaging. The abdomen was depilated with a hair removal cream to prevent air trapped in the fur from interfering with ultrasound coupling into the animal. Ultrasound coupling gel was applied to the depilated skin, and images of the prostate and neighboring anatomy were acquired through the ventral body wall in transverse and sagittal orientations. Ultrasound images were acquired using a commercial micro-imaging system (Vevo 660, VisualSonics, Inc., Toronto, ON). The system employs a single-element, 30 MHz center frequency probe that produces a 55°-115°-115 μm3 resolution volume at the 12.7-mm focal depth. Images were acquired with the region of interest centered at the focus. Two-dimensional images were acquired with 30-μm spacing by translating the ultrasound probe in the out-of-plane dimension using a linear motor. Three-dimensional images showing 12°-12°-9-mm3 volumes were reconstructed from the two-dimensional images and displayed in a dynamic cube view format. Three-dimensional image acquisition and reconstruction required approximately 30 s. The sagittal diameters of the tumors were measured using the electronic calipers of the 3-D ultrasound display software. For each tumor, the measured diameters were plotted as functions of time elapsed since the castration day. A computer program (SigmaPlot 2000) was used to compute linear diameter growth curves.

Results

Characterization of a Polyclonal Antibody Against Recombinant pTrcHis mPSP94

Figure 3:
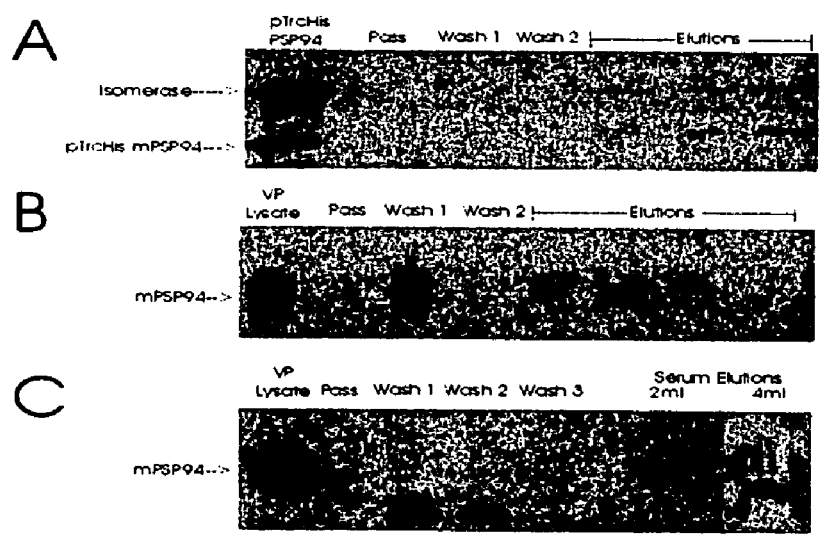
FIG. 3 illustrates western blots demonstration of the presence of mouse serum PSP94 via affinity column technique. All samples, including recombinant pTrcHis mPSP94 and natural mouse PSP94 from VP tissue lysate and serum in this figure, were purified using the affinity column. VP lysate positive controls were loaded from a 100 mg/ml standardized sample. (A) Western blots of pTrcHis mPSP94 by Affinity column. (B) Western blots demonstrating purification of the lysate of natural mouse PSP94 from ventral prostate tissue by affinity column. (C) Western blot demonstrating the presence of mouse PSP94 in the serum of wild type mice (2 ml and 4 ml serum samples used). The irregular bands observed for the different serum elutions are most likely due to high salt concentrations despite samples being desalted. Equivalent and comparable samples were loaded from each step of affinity column purification for each Western blot.

We have previously reported the production of several kinds of antibodies for mouse PSP94 studies, all of which lacked high titer and specificity (Thota, A. et al., J.Cell Biochem., 88: 999-1011, 2003). As shown in SDS-PAGE (FIG. 1A), according to the standard protocol utilizing the heavy metal affinity column provided by the manufacturer, two dominant protein bands were always co-purified at an apparent molecular weight of 20.8 kDa and 15 kDa separately. MSMALDI sequencing analysis was performed on these two purified proteins and both bands contained several histidine rich areas. Sequencing results observed by ESI-MS demonstrated that bands at 20.8 kDa and 15 kDa were isomerase and pTrcHis mPSP94 respectively (data not shown). Considering mouse PSP94 is a small-sized peptide (93 amino acids 10.6 kDa) of weaker antigenecity, we utilized the larger bacteria band (peptidyl-prolyl cis-trans isomerase from *E. coli*, 20.8 kDa) as a carrier protein, which should act the same as other GST (glutathione-S-transferase) fusion proteins we used 19, to elicit a stronger immune response. A higher dose of antigen (2.5 mg pTrcHis mPSP94/rabbit) was used to obtain polyclonal rabbit antiserum. Western blotting analysis demonstrated the antibody to be both sensitive and specific (FIGS. 1A & B) for isomerase and pTrcHis mPSP94. Western blot analysis was also conducted on natural mouse PSP94 from the ventral prostate lysate and found to be very specific (FIG. 1E and FIG. 3B). Since the antibody detected a wide band with smearing, a kit for the detection of glycosylation of the protein was used to study the same Western blots (FIG. 1C). A broad range of glycosylated mouse PSP94 proteins, shown as positive magenta bands, were observed (FIG. 1C), indicating the protein is heavily glycosylated (pTrcHis mPSP94 was used as a negative control). As a control, human PSP94 protein (10 μg) purified from human semen 26 was loaded for a comparison. FIG. 1D shows a Coomassie blue SDS-PAGE staining of the purified human PSP94 protein. Glycosylation detection for human seminal PSP94 (FIG. 1D) was negative.

De-glycosylation reaction was performed to confirm the glycosylation of mouse PSP94 from prostate tissue lysates. Western blots (FIG. 2C) showed a stronger band with lower molecular weight (14.3 Kb) after deglycosylation, probably due to focusing of the de-glycosylated PSP94 protein.

Down Regulation of the Prostate Tissue PSP94 Expression is Associated with Different Tumor Grades as Demonstrated by Immunohistochemistry (IHC):

The antibody for pTrcHis mPSP94 was further characterized via IHC staining and found to be specific for the cytoplasm of the endothelial cells of the prostate gland (FIG. 2). No stromal staining was detected. PSP94 expression was tested in 100 different tissue fixed blocks from adult mice of different tumor grade (i.e., wild type (n=11), low grade mPIN (n=19), high-grade mPIN (n=23), and well (n=22), moderately (n=18), and poorly differentiated (n=15) CaP) and genetically engineered lines (TGMAP and KIMAP). Strong positive staining intensity (2+) was found primarily in normal glandular tissue, (LG) low-grade mPIN, and HG (high grade) mPIN foci. Strong positive staining, however, could also be found in WDCaP and MDCaP with a decreasing incidence respectively (Table 1).

an affinity column using the polyclonal PSP94 antibody described above was established. The column was then used to purify recombinant pTrcHis mPSP94 in order to demonstrate column activity. FIG. 3A demonstrates that recombinant protein was purified with a high yield and little to no protein was lost in the pass and wash. Since equivalent amounts of samples were loaded in the gel, the addition of each elution represents the final column yield. Next, PSP94 from mouse ventral prostate lysates was passed through the column to determine if the column could purify natural mouse PSP94 (FIG. 3B). The column successfully purified mouse PSP94 with a yield of roughly 40%. Little to no mouse PSP94 was observed in the column pass; however, a substantial amount was noted in the first column wash. Finally, 2 ml and 4 ml of wild type mouse serum were passed through the column, and mouse PSP94 was eluted (FIG. 3C). Column passes and washes yielded no mouse PSP94 but did have some non-specific protein, most likely due to the high protein content of serum. VP lysate mouse PSP94 band was used as a positive control and was found to match up with serum elutions. Furthermore, increasing amounts of mouse PSP94 were noted for larger sample sizes of serum.

TABLE 1

Table 1. Association of mouse PSP94 immunoreactivity (intensity/extent) with tumor grades in genetically engineered mouse prostate cancer

| | WT (%) | LGmPIN (%) | HGmPIN (%) | $P_1$ | WDCaP (%) | MDCaP (%) | PDCaP (%) | $P_2$ | P |
|---|---|---|---|---|---|---|---|---|---|
| | | | | PSP94 intensity | | | | | |
| 0 | 0 | 0 | 0 | 0.886 | 0 | 1 (5) | 2 (20) | 0.004 | 0.000 |
| 1+ | 2 (18.2) | 4 (21.1) | 4 (15.4) | | 13 (59.1) | 18 (90) | 8 (80) | | |
| 2+ | 9 (81.8) | 15 (78.9) | 22 (84.6) | | 9 (40.9) | 1 (5) | 0 | | |
| | | | | PSP94 extent | | | | | |
| 0% | 0 | 0 | 0 | 0.145 | 0 | 1 (5) | 2 (20) | 0.062 | 0.003 |
| 1-25% | 1 (9.1) | 0 | 0 | | 0 | 1 (5) | 0 | | |
| 26-50% | 1 (9.1) | 1 (5.3) | 1 (3.8) | | 2 (9.1) | 5 (25) | 2 (20) | | |
| 51-75% | 5 (45.5) | 5 (26.3) | 4 (15.4) | | 7 (31.8) | 10 (50) | 3 (30) | | |
| 76-100% | 4 (36.4) | 13 (68.4) | 21 (80.8) | | 13 (59.1) | 3 (15) | 3 (30) | | |

*Pearson Chi-square test was used to determine significant difference between tumor grades. The numbers in brackets represent the percentage of tumors for that specific grade with that specific intensity/extent. $P_1$ values are a test for significant difference in intensity and extent between WT, LGPIN, and HGPIN tissues. $P_2$ values are a test for a significant difference in intensity and extent between WDCaP, MDCaP, and PDCaP tumors. Finally, P test for a significant difference in intensity and extent between all tumor grades.

Conversely, PDCaP, MDCaP, and WDCaP had a higher incidence of weak and negative staining (1+ and 0). Chi-square tests revealed a significant difference in the intensity between all grades (P<0.01) as well as in the intensity of CaP tissues only (P2=0.004, Table 1). There was, however, no significant difference in the intensity of wild type, LGmPIN, and HGmPIN tissues (P1=0.886, Table 1). These data suggest that PSP94 expression decreases as CaP progresses, possibly due to the "leaking out" of PSP94 into the surrounding vasculature. The extent of staining was also noted among the different tissues, and was significantly different between all grades (P=0.003, Table 1). However, no significant difference in staining extent was noted among the non-CaP tissues and the CaP tissues (P1=0.145 and P2=0.062).

Figure 4:
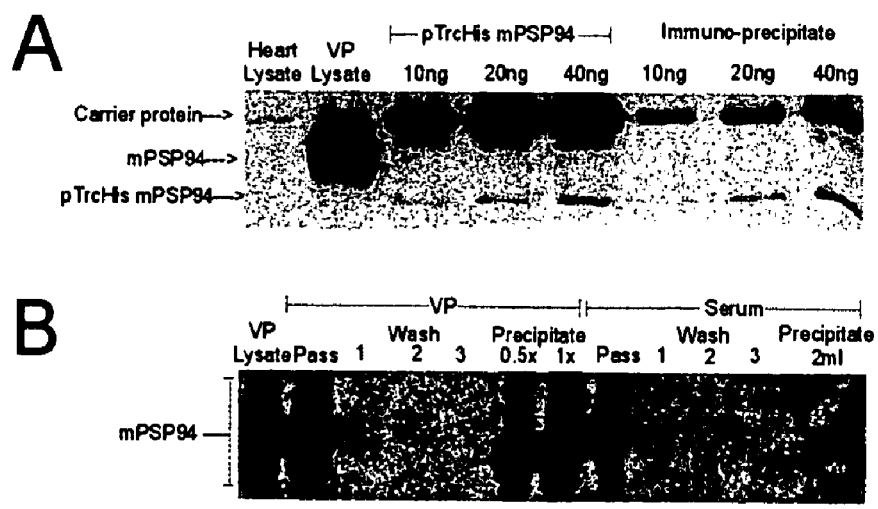
FIG. 4 illustrates the demonstration of the presence of mouse serum PSP94 via immuno-precipitation techniques. Western blot analysis was performed for the recombinant pTrcHis mPSP94 and natural mouse PSP94 from tissue lysate and serum. All samples were precipitated using the same polyclonal mouse PSP94 antibody used for the affinity column. VP lysate positive controls were loaded from a 100 mg/ml standardized sample. (A) Western blot demonstrating the immuno-precipitation technique works properly with the recombinant pTrcHis mPSP94 with a good yield. (B) Western blots demonstrating that the precipitation technique works for natural mouse PSP94 and also detects the presence of mouse PSP94 in the serum of wild type mice (2 ml serum used). Equivalent and comparable samples were loaded in each well for each Western blot.

Demonstration of the Presence of Mouse PSP94 in the Serum of Wild Type Mice by Affinity Column Separation and Purification:

Next we intend to test, as with in human PSA and PSP94, whether the decreased expression in mouse prostate tumor tissues results in increased levels of serum PSP94. At first, in order to demonstrate the presence of mouse PSP94 in serum, Further Demonstration of the Presence of Mouse Serum PSP94 by Immunoprecipitation Experiments:

Further demonstration of the existence of PSP94 in mouse serum was by immunoprecipitation experiments. The same logical steps were taken as in affinity column, producing the same results (FIG. 4). First, recombinant pTrcHis mPSP94 was precipitated to demonstrate the technique was working properly (FIG. 4A). Serial dilutions were precipitated with a high yield from samples of 10 ng, 20 ng, and 40 ng (isomerase was precipitated along with mouse PSP94). Second, natural mouse PSP94 was precipitated from ventral prostate lysate (FIG. 4B). Like in affinity column, substantial amounts of mouse PSP94 washed off in the pass and first wash, however, a significant amount was visible in the precipitate. In the same blot, 2 ml of serum was precipitated. Due to the high protein content of serum, the pass had significant nonspecific background. No mouse PSP94 was detected in the subsequent washes and the precipitate revealed the multi-band mouse PSP94. The multiple bands observed for immuno-precipitation and not Affinity column purification may be due to the fact that in immuno-precipitation the antibody is free in solution and may bind to PSP94 differently. Glycosylation of mPSP94 may also play a role in this phenomenon. Both affinity column and immuno-precipitation produced comparable amounts of mouse PSP94 precipitate for 2 ml of serum.

Establishment of Competitive ELISA Standard Curves Using Recombinant pTrcHis Mouse PSP94 as Coating Antigen:

In order to demonstrate that mouse serum PSP94 is quantifiable, two sets of immunoassays were performed for obtaining standard curves that will quantify serum mouse PSP94 levels, as well as demonstrate the assay is functional for natural mouse PSP94. The first standard graph utilized recombinant pTrcHis mPSP94 as both the coating antigen and the competitor (FIG. 5A). This assay consistently produced a linear logarithmic graph with a negative slope, indicating the assay was working. The next step was to confirm the sensitivity of the assay applied to natural mouse PSP94. FIG. 5B is an example of the resultant standard curve when using recombinant pTrcHis mPSP94 as the coating antigen, and mouse PSP94 from the ventral prostate lysate as the competitor. This standard graph produced no slope and demonstrated the assay could not distinguish between different levels of mouse PSP94. It was thought that since the carrier protein isomerase most likely produced the most antibodies in our polyclonal antibody, it was overpowering our immunoassay. This was not noticed in our standard graph using recombinant pTrcHis mPSP94 as the competitor because, in that case, isomerase coated to the plate had competition. Consequently, $E.\ coli$ lysate containing isomerase was used to block our polyclonal antibody and remove any signal produced by isomerase competition. Two new standard curves (FIGS. 5C & D) were generated using this technique. Again, using pTrcHis as the competitor, the assay produced a linear graph with a negative slope (FIG. 5C). The same results were obtained when using the VP lysate (natural mouse PSP94) as the competitor, indicating the assay was functional for detecting mouse PSP94 (FIG. 5D). This new assay using $E.\ coli$ lysate to block out isomerase activity was consequently used to quantify mouse PSP94 in our unknown serum samples.

Figure 6:
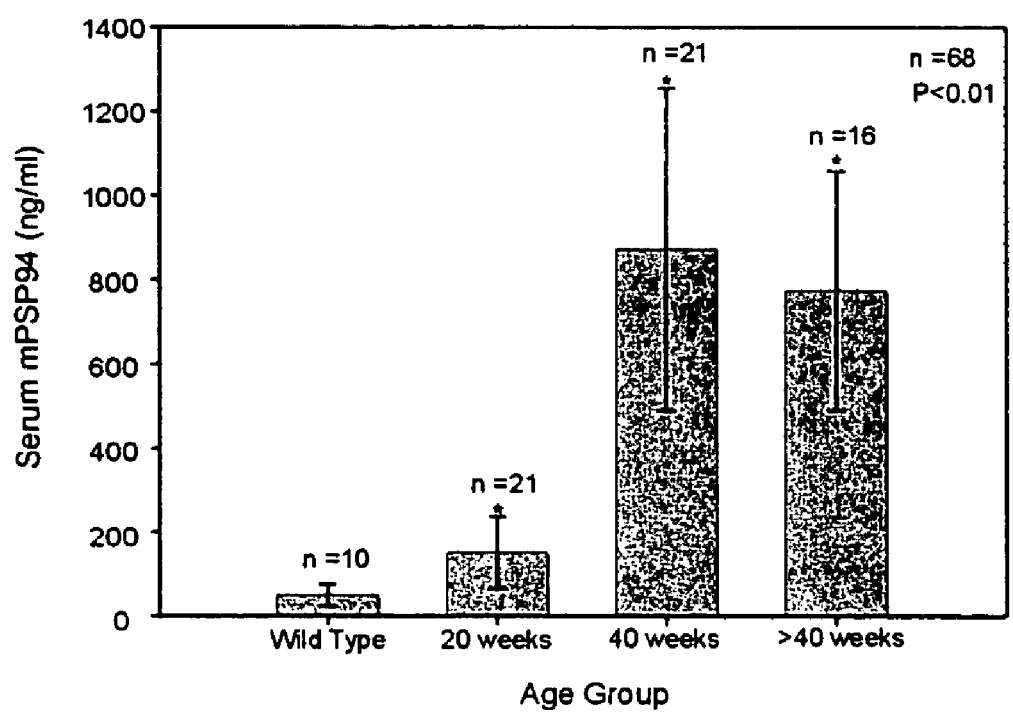
FIG. 6 illustrates Average serum mouse PSP94 levels for KIMAP mice from different age groups. Sixty-eight serum levels from various KIMAP mice were calculated via interpolation from a standard graph (FIG. 5C) of known levels of recombinant pTrcHis mPSP94. Error bars represent standard deviations and * indicates P<0.01 compared to wild type mouse PSP94 levels.

Quantification of Mouse PSP94 in Serum from Mice of Different Age Groups Via Established Competitive ELISA Techniques:

From the established standard graph technique (FIG. 5C), serum mouse PSP94 levels were quantified (FIG. 6). In our system, 50 µl of serum separated from living mouse tail blood were assayed by ELISA for each well. Average serum levels for wild type mice were 49.8 ng/ml. Average serum levels for KIMAP mice of 20, 40, and >40 weeks were 150.9 ng/ml, 835.5 ng/ml, and 774.8 ng/ml respectively. As compared with wild type mice, serum PSP94 levels increase significantly ($P<0.001$) with age in KIMAP mice until 40 weeks of age. This increase is synchronous to increases of grades from well- to moderately-differentiated CaP in our KIMAP model. No significant difference was noted between 40 and >40 week KIMAP mice groups ($P=0.143$).

Figure 7:
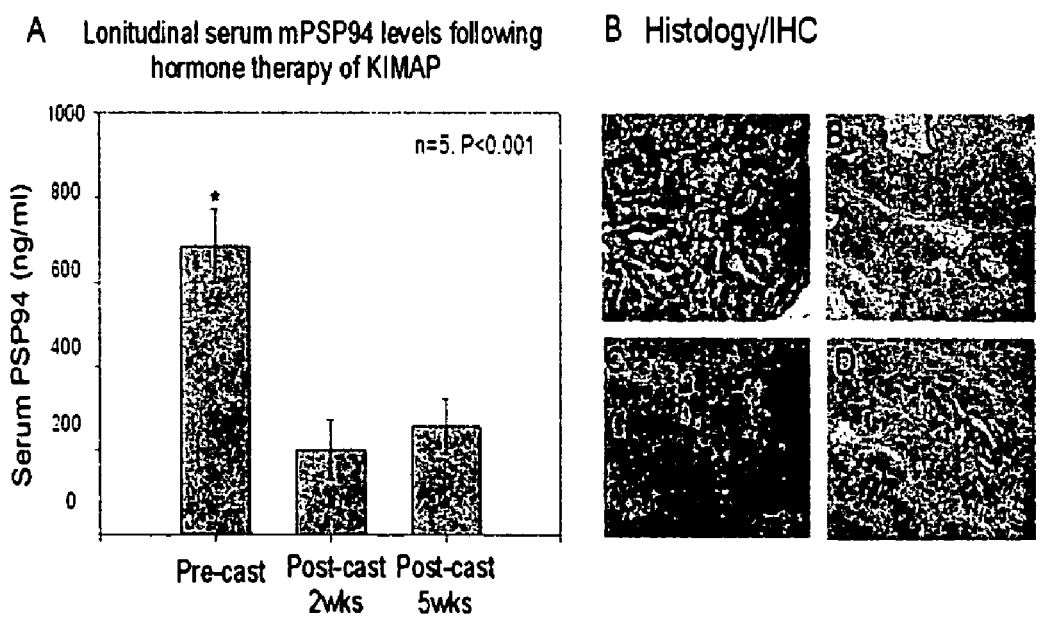
FIG. 7 illustrates serum mPSP94 levels before and after androgen deprivation therapy for KIMAP mice (n=5) along with histological analysis. (A) Serum mPSP94 levels (ng) pre and post castration demonstrating a significant reduction in response to therapy (P=0.001). (B) Histological analysis of prostate demonstrating involution of gland structure and altered PSP94, and androgen receptor (AR) expression (10× magnification). (A & B) H&E staining of tissue samples from KIMAP mouse prostate before and after castration respectively. Increased stroma to gland ratio is evident in B. (C) AR expression post castration. (D) PSP94 expression post-castration.
Figure 8:
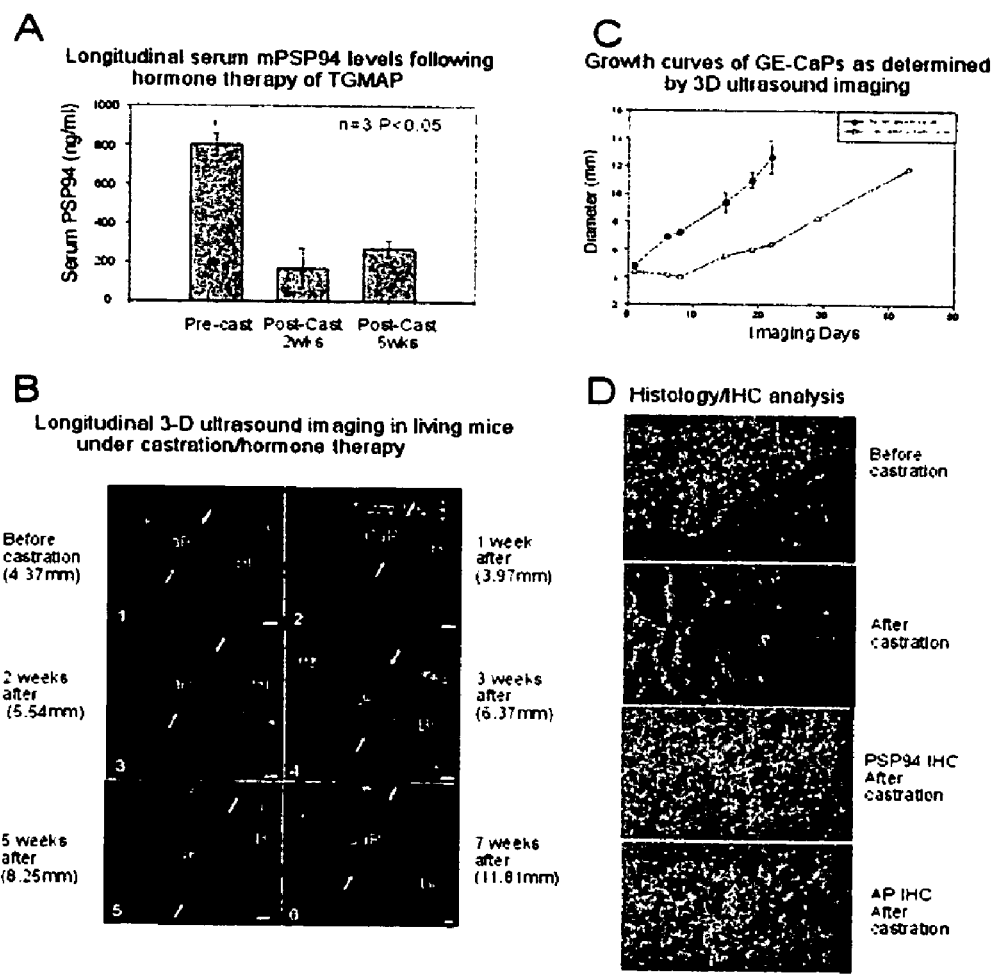
FIG. 8. Combined tests of mouse serum PSP94 levels and 3-D ultrasound imaging before and after androgen deprivation therapy (castration) for TGMAP mice at late stage of GECaP development. (A) Serum mPSP94 levels (ng) pre and post castration demonstrating a significant reduction in response to therapy followed by refractory (n=3, P<0.05). (B) Longitudinal detection by 3-D ultrasound imaging in living castrated mice with rapid VP tumor development. Panels 1 through 6 show representative two-dimensional slices from six different 3-D ultrasound images before castration and at different time points after castration. Panel 1: The mouse was 21 weeks old when the tumor was first detected (measuring 4.37 mm in diameter) and was then castrated (Day 1). The next 5 panels revealed the same tumor on Days 8, 15, 22, 29 and 43 as the tumor diameter went from 3.97 to 5.54, 6.37, 8.25 and 11.81 mm respectively. The ventral surface of the abdominal wall is shown at the top of the image, while the deeper abdominal and retroperitoneal structures are at the bottom of the image. Scale size in the 3-D ultrasound images is 1 mm. CaP and BI indicate prostate and bladder position respectively. (C) Determination of growth curve in PSP-TG-MAP mice based on 3-D ultrasound imaging data of B. Rapid tumor growth rate is shown in this graph for transgenic mice with GE-CaPs. The control group was PSP-TGMAP mice (n=3) without castration. The maximum sagittal diameter of the tumor was plotted against the day post initial observation/castration. (D) Histological analysis of the castrated prostate tissues demonstrating involution of gland structure and altered PSP94, and androgen receptor expression (10× magnification). Before castration was from the age matched, late stage of CaP in TGMAP mice. Involution in the prostate tissue under castration was evident. IHC analysis of the prostate tissue demonstrated weak PSP94 and AR (androgen receptor expression) in poorly differentiated CaP.

Demonstration of Utility of Serum PSP94 Marker to Monitor Hormone Therapy (Castration) in GE-CaP Mouse Models:

In order to demonstrate utility of serum PSP94 in pre-clinical trial studies, PSP94 levels were tested for their responsiveness and refractory to androgen deprivation therapy to mice with GE-CaPs in our transgenic (PSP-TGAMP) and knock-in (PSPKIMAP) mouse prostate cancer models. Castration was used for mimicking hormone therapy in two groups of mice with CaP. The first group was used to test for tumors in well- and moderately-differentiated CaP development (not at the late stage of CaP development with massive metastasis) in our recently established knock-in prostate cancer (PSP-KIMAP) model, which revealed features similar to human CaP. Five PSP-KIMAP mice at the age of 10 months were subjected to orchidectomy operation (via scrotum access). Tail blood samples were collected prior to castration, and then 2 and 5 weeks after castration. As shown in FIG. 7, there is a significant decrease in serum PSP94 levels ($P<0.001$) post castration. Histological analysis of prostate tissue from the castrated mice demonstrated significant involution as a result of the androgen deprivation. IHC analysis for androgen receptor (AR) and PSP94 demonstrated a reduction in expression compared to non-castrated mice (FIG. 1B). Since AR staining was still present (FIG. 7B), the observed PSP94 expression may be attributed to testosterone secreted from the adrenal gland. To test for refractory of hormone therapy in pre-clinical trials, GE-CaP mice at later stages of CaP with large tumor mass were selected for hormone therapy (castration). Only PSP-TGMAP mice were selected. A new method developed in our laboratory for acquisition and analysis of 3-D ultrasound images of mouse prostate cancer models 30 was employed to assist the diagnosis by PSP94 serum marker. This is because of the following considerations: (1) PSP-TGMAP mice revealed exuberant tumor growth with neuroendocrine (NE) features (as did the TRAMP and LADY models), which the GECaP tumor mass could reach extraordinary sizes of up to 15 grams/35 body weight in just 2 weeks time; (2) Our UACC protocols mandate a 2-weeks time interval limit for collecting tail blood and more frequent collection is not possible; (3) It is important to assess effectiveness of the serum marker, if longitudinal imaging (every other day) observation and the determination of the growth curve of the GE-CaPs in the living animals of castration transgenic mice are to be simultaneously performed. A total of three mice were castrated and two were imaged. FIG. 8A illustrates that serum levels of PSP94 in castrated mice decreased 2 weeks after castration, and then stabilized at a higher level than normal. This may indicate the incomplete responsiveness or incomplete cure of CaP after castration. Furthermore, longitudinal 3-D ultrasound imaging of a castrated mouse in FIG. 8B revealed that the tumor decreased slightly in size from 4.37 to 3.97 mm in diameter (FIG. 8B row 1) 1 week after castration. Continual tumor expansion was observed in 3-D imaging (panel rows 2-3) from 1 to 7 weeks after castration. Based on the longitudinal imaging data and measurements of tumor diameters, a tumor growth curve was established (FIG. 8C), along with non-castrated mice (n=3) as a control. The growth curve demonstrates that castration (hormone therapy) in mice with late stages of CaP slowed and delayed the rapid tumor growth rate and increased survivability. Responsiveness to castration (hormone therapy) was slight and brief (first week after castration), which is consistent with the results from the serum PSP94 tests (FIG. 8A). Histological analysis (FIG. 8D) also demonstrated that in castrated mice, even in poorly differentiated CaP tissues, atrophy is evident, which is the reason for increased survivability (FIG. 8C). IHC experiments with several CaP marker genes (AR and PSP94) were performed in order to further demonstrate that the androgen therapy was, in fact, working. The expression levels for each of the two markers used were decreased when compared to the levels of GE-CaP mice with the same cancer grade (FIG. 8D).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A recombinant rodent serum marker for prostate cancer, which comprises the following amino acid sequence:

(SEQ ID NO: 1)
MGGSHHHHHGMASMTGGGGMGRNTRYDDDDKDRWGSWVCSIENREIFPN
QMSDDCMDADGNKHFLNTPKKNCTWCSCDKTSITCCTNATPLSYDKDNCD
NQFHPENCTYSVVDRKNPGKTCRVDSWTM.

* * * * *

SEQUENCE LISTING

<160> NUMBER OF SEQ ID NOS: 1

<210> SEQ ID NO 1
<211> LENGTH: 129
<212> TYPE: PRT
<213> ORGANISM: Artificial Sequence
<220> FEATURE:
<223> OTHER INFORMATION: antigenic sequence

<400> SEQUENCE: 1

```
Met Gly Gly Ser His His His His His Gly Met Ala Ser Met Thr
1               5                   10                  15

Gly Gly Gly Gly Met Gly Arg Asn Thr Arg Tyr Asp Asp Asp Lys
            20                  25                  30

Asp Arg Trp Gly Ser Trp Val Cys Ser Ile Glu Asn Arg Glu Ile Phe
            35                  40                  45

Pro Asn Gln Met Ser Asp Asp Cys Met Asp Ala Asp Gly Asn Lys His
        50                  55                  60

Phe Leu Asn Thr Pro Lys Lys Asn Cys Thr Trp Cys Ser Cys Asp Lys
65                  70                  75                  80

Thr Ser Ile Thr Cys Cys Thr Asn Ala Thr Pro Leu Ser Tyr Asp Lys
            85                  90                  95

Asp Asn Cys Asp Val Gln Phe His Pro Glu Asn Cys Thr Tyr Ser Val
            100                 105                 110

Val Asp Arg Lys Asn Pro Gly Lys Thr Cys Arg Val Asp Ser Trp Thr
        115                 120                 125

Met
```